US010930175B1

(12) United States Patent
Morrison, III

(10) Patent No.: US 10,930,175 B1
(45) Date of Patent: Feb. 23, 2021

(54) CPR TRAINING DEVICE

(71) Applicant: RayLynn Products, LLC, Grove City, OH (US)

(72) Inventor: Charles Ray Morrison, III, Reynoldsburg, OH (US)

(73) Assignee: RAYLYNN PRODUCTS, LLC, Grove City, OH (US)

( * ) Notice: Subject to any disclaimer, the term of this patent is extended or adjusted under 35 U.S.C. 154(b) by 0 days.

(21) Appl. No.: 16/889,911

(22) Filed: Jun. 2, 2020

Related U.S. Application Data

(62) Division of application No. 14/594,517, filed on Jan. 12, 2015, now Pat. No. 10,777,098.

(51) Int. Cl.
| | |
|---|---|
| G09B 23/02 | (2006.01) |
| G09B 23/28 | (2006.01) |
| A61M 16/10 | (2006.01) |
| A62B 23/02 | (2006.01) |
| B01D 29/01 | (2006.01) |
| A61M 16/00 | (2006.01) |
| A62B 18/02 | (2006.01) |

(52) U.S. Cl.
CPC ....... *G09B 23/288* (2013.01); *A61M 16/0048* (2013.01); *A61M 16/1055* (2013.01); *A62B 18/025* (2013.01); *A62B 23/02* (2013.01); *B01D 29/012* (2013.01)

(58) Field of Classification Search
None
See application file for complete search history.

(56) References Cited

U.S. PATENT DOCUMENTS

| | | | |
|---|---|---|---|
| 3,386,585 A | 6/1968 | Weyand et al. | |
| 3,782,083 A | 1/1974 | Rosenberg | |
| 4,790,327 A * | 12/1988 | Despotis | A61M 16/0488 |
| | | | 128/205.23 |
| 4,802,857 A * | 2/1989 | Laughlin | G09B 23/288 |
| | | | 434/265 |
| 5,005,568 A * | 4/1991 | Loescher | A61M 16/208 |
| | | | 128/202.28 |
| 5,121,745 A | 6/1992 | Israel | |
| 5,337,739 A | 8/1994 | Lehman | |
| 6,131,573 A * | 10/2000 | Brown | A61B 5/097 |
| | | | 128/202.28 |
| 7,993,071 B2 | 8/2011 | Clawson | |
| 2002/0100475 A1 * | 8/2002 | McKinney | A61M 16/0048 |
| | | | 128/203.11 |

* cited by examiner

*Primary Examiner* — James B Hull
(74) *Attorney, Agent, or Firm* — Ronald J. Koch; The Eley Law Firm

(57) ABSTRACT

A CPR training device is disclosed comprising a first member including a mouthpiece portion and a first engaging portion, a second member including an output portion and a second engaging portion, and an air passageway. The first engaging portion and the second engaging portion cooperates to form a filter seating arrangement at a filter seat position when assembled together to secure a filter within the CPR training device. The air passageway is open to air outside of the CPR training device only through the mouthpiece portion and the output portion. The filter is disposed in the air passageway at the filter seat position.

11 Claims, 9 Drawing Sheets

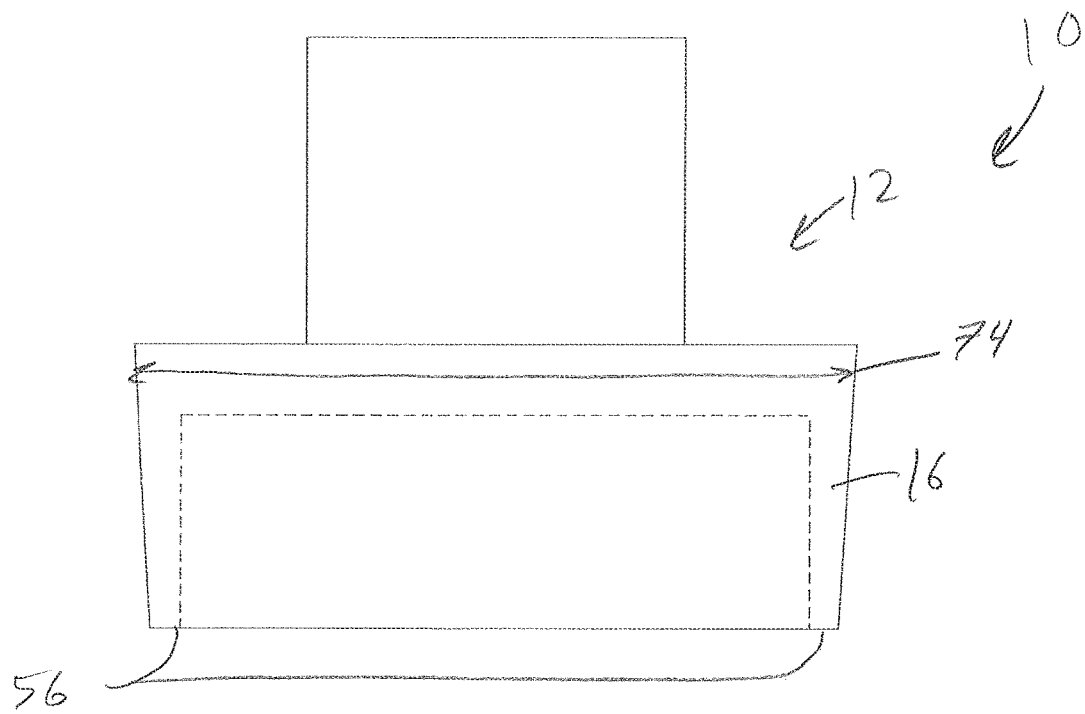
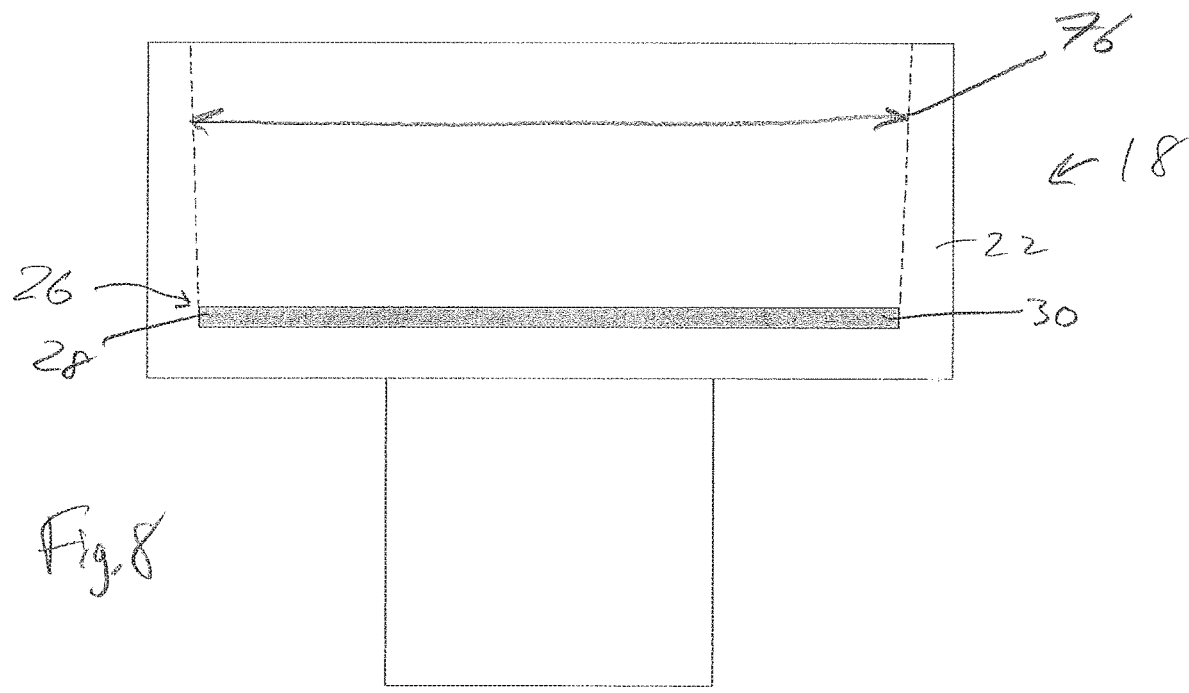
Fig. 8

CPR TRAINING DEVICE

CROSS-REFERENCE TO RELATED APPLICATIONS

This application is a divisional of U.S. patent application Ser. No. 14/594,517, filed Jan. 12, 2015, the contents of which are incorporated by reference herein.

BACKGROUND

Cardiopulmonary resuscitation (CPR) is a technique used in emergencies in which a person's breathing or heartbeat has stopped. The technique includes a CPR performer forcing air into the lungs of a CPR recipient. The CPR performer often covers the mouth of the CPR recipient with a CPR mask and blows air through a valve connected to the CPR mask. The valve includes a bypass port to protect the CPR performer by allowing vomit, disease, and other harmful substances to flow through the bypass rather than contact the CPR performer, while still permitting air intake by the CPR recipient from the CPR performer.

CPR training includes the use of masks and valves to simulate CPR technique on CPR manikins. While a bypass in the CPR valve is not necessary in CPR training, a training CPR valve should be as realistic as possible with an amount of backpressure equivalent to a CPR valve for effective CPR training. Further, the risk of germ contamination of the CPR manikins and training valves is great because multiple trainees often use the same CPR manikins and training valves. There exists a need for a CPR training device and method of using a CPR training device that allows effective CPR simulation while preventing the transmission of germs during CPR training.

SUMMARY

In accordance with aspects of the present disclosure, a CPR training device is disclosed. The CPR training device includes a first member including a mouthpiece portion and a first engaging portion, a second member including an output portion and a second engaging portion, and an air passageway. The first engaging portion and the second engaging portion cooperate to form a filter seating arrangement at a filter seat position when assembled together to secure a filter within the CPR training device. The air passageway is open to air outside of the CPR training device only through the mouthpiece portion and the output portion. The filter is disposed in the air passageway at the filter seat position.

In accordance with aspects of the present disclosure, a CPR training device is disclosed. The CPR training device includes a first member including a mouthpiece portion and a first engaging portion, a second member including an adapter portion, a second engaging portion, and a filter seat portion, an air passageway open to air outside of the CPR training device only through the mouthpiece portion and the output portion, a filter disposed in the air passageway at the filter seat portion, and a CPR mask attached to the adapter portion. The first engaging portion and the second engaging portion engage to secure the filter within the CPR training device.

In accordance with aspects of the present disclosure, a method of using a CPR training device is disclosed. The method includes providing a CPR training device having a first member detachably coupled to a second member and a first filter disposed within the CPR training device to a CPR trainee, permitting the CPR trainee to simulate a CPR event with the CPR training device, separating the first member from the second member, discarding the first filter, cleaning the first member and the second member, coupling the first member to the second member with a second filter disposed within the CPR training device.

BRIEF DESCRIPTION OF THE DRAWINGS

The embodiments described herein and other features, advantages, and disclosures contained herein, and the manner of attaining them, will be better understood from the following description in conjunction with the accompanying drawing figures, in which like reference numerals identify like elements, and wherein:

1 is a perspective view of a CPR training device according to an embodiment of the present disclosure;

FIG. 8 is an exploded view of a CPR training device according to an embodiment of the present disclosure.

DETAILED DESCRIPTION

In the following detailed description of embodiments of the present disclosure, reference is made to the accompanying drawings that form a part hereof, and in which is shown by way of illustration, and not by way of limitation, such specific embodiments. It is to be understood that other embodiments may be utilized and that changes may be made without departing from the spirit and scope of the present disclosure.

Figure 1:
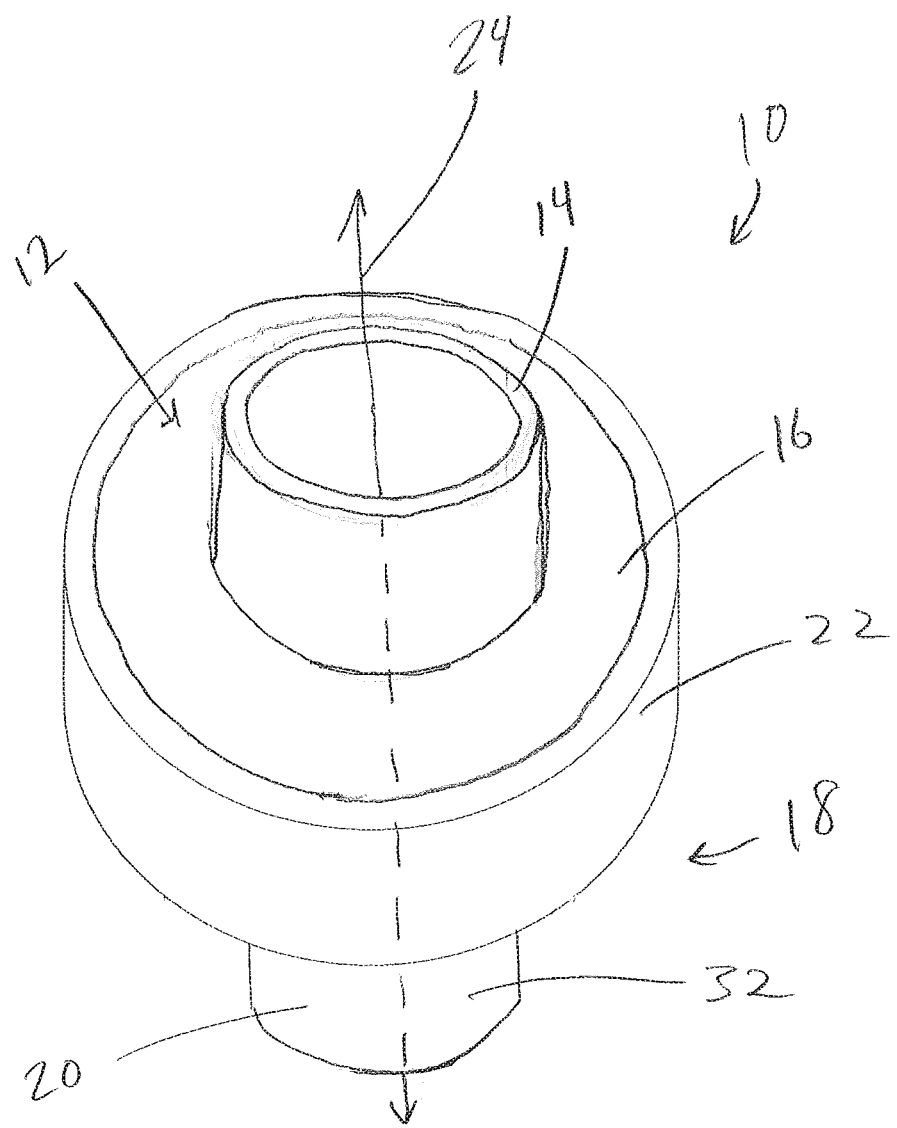

Reference is now made to FIG. 1, which shows a CPR training device 10 of an embodiment of the present disclosure in an assembled state. The device 10 includes a first member 12 having a mouthpiece portion 14 and a first engaging portion 16. The device 10 further includes a second member 18 having an output portion 20 and a second engaging portion 22. The output portion 20 of an embodiment is also referred to as an adapterportion 32. The device 10 of the embodiment shown in FIG. 1 further includes an air passageway 24 extending at least from the mouthpiece portion 14 to the output portion 20.

Figure 2:
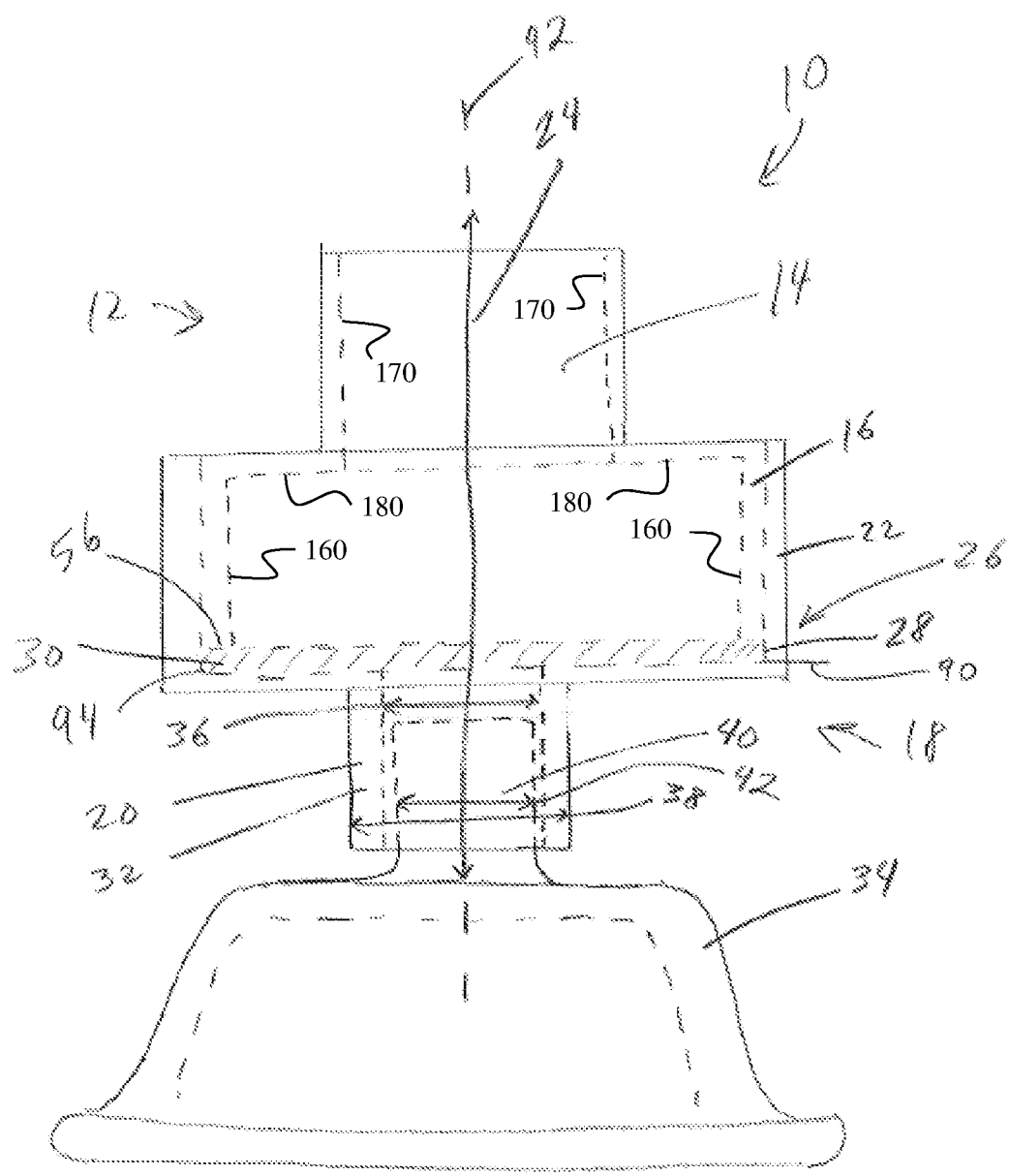
FIG. 2 is a side elevation view of a CPR training device according to an embodiment of the present disclosure.

Referring now to FIG. 2, the device 10 of an embodiment includes the first engaging portion 16 and the second engaging portion 22 cooperating to form a filter seating arrangement 26 at a filter seat position 28 when the first engaging portion 16 and the second engaging portion 22 of the device 10 are assembled together to secure a filter 30 within the CPR training device 10. As illustrated in the embodiment of FIG. 2, the air passageway 24 is open to air outside of the CPR training device 10 only through the mouthpiece portion 14 and the output portion 20. The filter 30 is disposed in the air passageway 24 at the filter seat position 28. In one embodiment, the air passageway 24 is linear and is substantially at a right angle to the plane of the filter 30.

In one or more embodiments, the filter 30 comprises a paper material. In one or more embodiments, the filter 30 comprises a fabric material. An embodiment includes the filter 30 being a HEPA style filter. The filter 30 prevents contamination originating from a person using the device 10 from entering a CPR training lung, such as a manikin lung. Further, the filter 30 prevents contaminants already in the lung from reaching the person using the device 10.

In one or more embodiments, a CPR mask 34 is attached to the output portion 20 or adapter portion 32. As shown in the embodiment of FIG. 2, the output portion 20 or adapter portion 32 includes an inner diameter 36 and an outer diameter 38. Further, the CPR mask 34 of an embodiment includes an orifice 40 having an outer diameter 42. The output portion 20 or adapter portion 32 of the FIG. 2 embodiment is sized to engage the outer diameter 42 of the CPR mask orifice 40. In one embodiment, both the outer diameter 42 of the CPR mask orifice 40 and the inner diameter 36 of the output portion 20 or adapter portion 32 is 15 millimeters to allow a press fit of the CPR mask 34 onto the output portion 20 or adapter portion 32.

Figure 3:
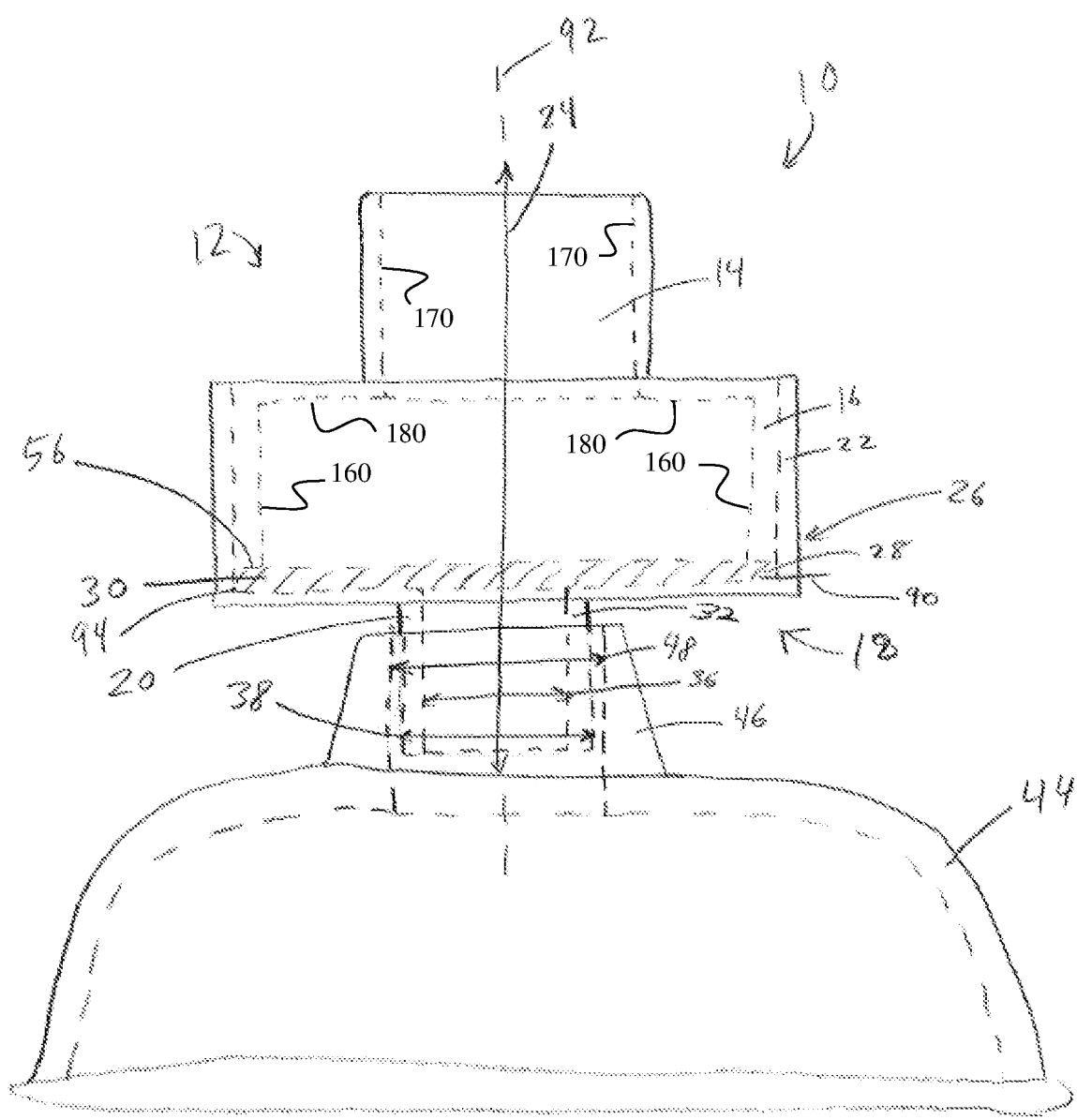
FIG. 3 is a side elevation view of a CPR training device according to an embodiment of the present disclosure.

Referring now to FIG. 3, a CPR mask 44 of an embodiment includes an orifice 46 having an inner diameter 48. The output portion 20 or adapter portion 32 of the FIG. 3 embodiment is sized to engage the inner diameter 48 of the CPR mask orifice 46. In one embodiment, both the inner diameter 48 of the CPR mask orifice 46 and the outer diameter 38 of the output portion 20 or adapter portion 32 is 22 millimeters to allow a press fit of the CPR mask 44 onto the output portion 20 or adapter portion 32. One or both of the inner diameter 36 and the outer diameter 38 of one or more embodiments is tapered for ease of assembly with one of the masks 34, 44. In another embodiment, the taper of the inner diameter 36 and the outer diameter is between one and three degrees.

As shown in the embodiments of FIGS. 2 and 3, the filter 30 is ultimately secured within the CPR training device 10 at an end surface 56 of the first engaging portion 16. A filter seat position 28 is disposed along a plane 90 perpendicular to an axis 92 extending through the mouthpiece portion 14 and the output portion 20 or adapter portion 32 when the first engaging portion 16 and the second engaging portion 22 are engaged. In the embodiments shown in FIGS. 2 and 3, the second engaging portion 22 comprises a filter seat portion 94, and the filter 30 is secured between the first engaging portion 16 and the filter seat portion 94. The device 10 of additional embodiments includes the first member 12 having one or more of the output portion 20 or adapter portion 32 and the second engaging portion 22 and the second member having one or more of the mouthpiece portion 14 and the first engaging portion 16. The device 10 further includes a second member 18 having an output portion 20 and a second engaging portion 22. In one embodiment, the first engaging portion 16 and the second engaging portion 22 are shaped and fit together so as to pinch the filter 30 between them so as to maintain a relatively sealed circumferential portion of the filter so as to better direct and maintain air flow through rather than around the filter 30. In this way, the CPR training device 10 with captured filter 30 best approximates the resistance of a standard CPR valve.

In another embodiment, the first member 12 and the second member 18 are at least semi-transparent to allow inspection of the filter 30 and the air passageway 24. In one or more embodiments, one or both of the first member 12 and the second member 18 are opaque or partially opaque and include any color or markings suitable for use or indication to the user or members of the general public.

Figure 4:
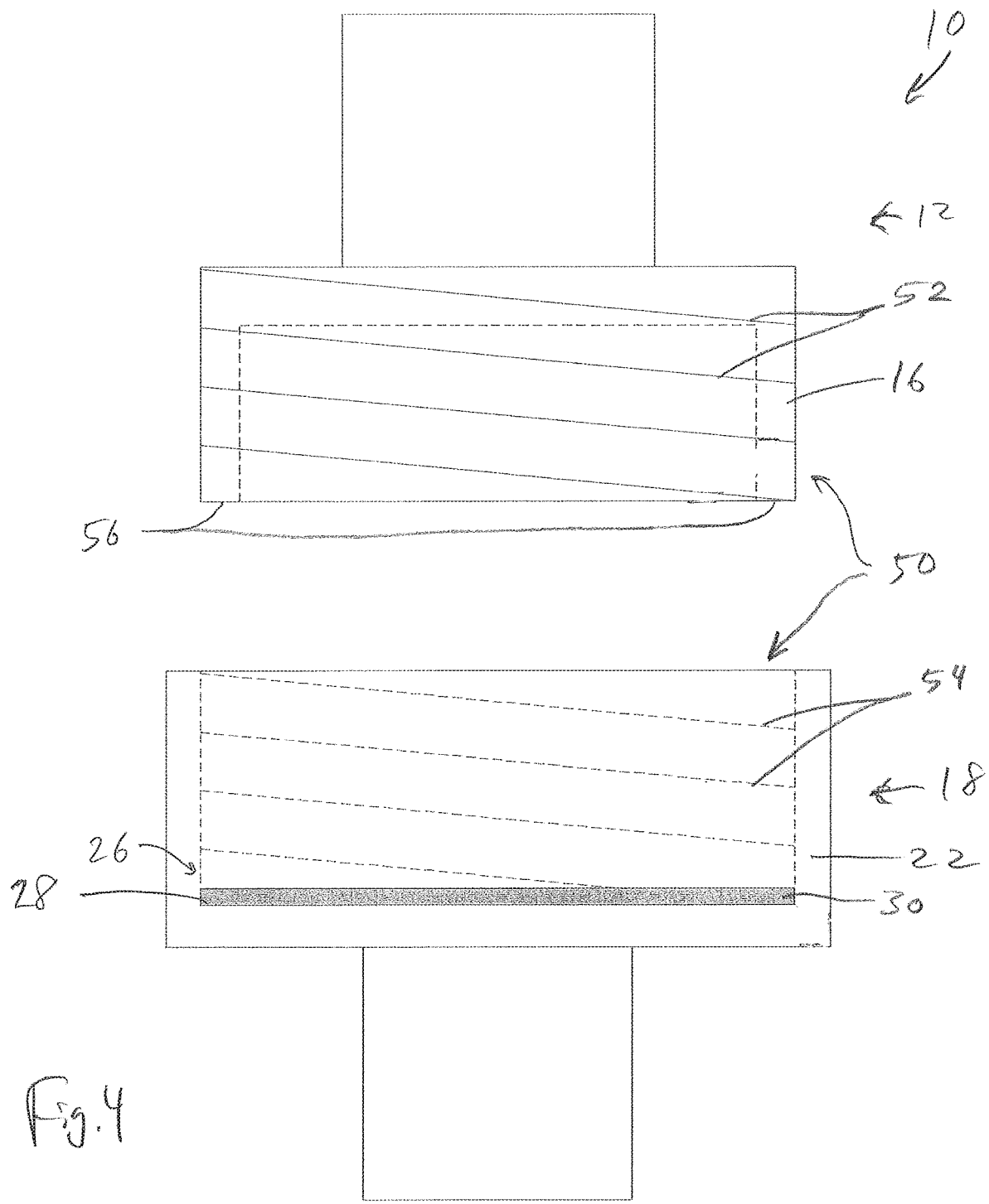
FIG. 4 is an exploded view of a CPR training device according to an embodiment of the present disclosure.

Reference is now made to FIG. 4, which shows an embodiment of the device 10. As shown in FIG. 4, the first engaging portion 16 and the second engaging portion 22 include helical threads 50. The first engaging portion 16 includes inner helical threads 52 and the second engaging portion 22 includes outer helical threads 54 that are complimentary to the inner helical threads 52. The first engaging portion 16 and the second engaging portion 22 form the filter seating arrangement 26 at the filter seat position 28 when the first engaging portion 16 and the second engaging portion 22 of the device 10 are rotated into each other.

Figure 5:
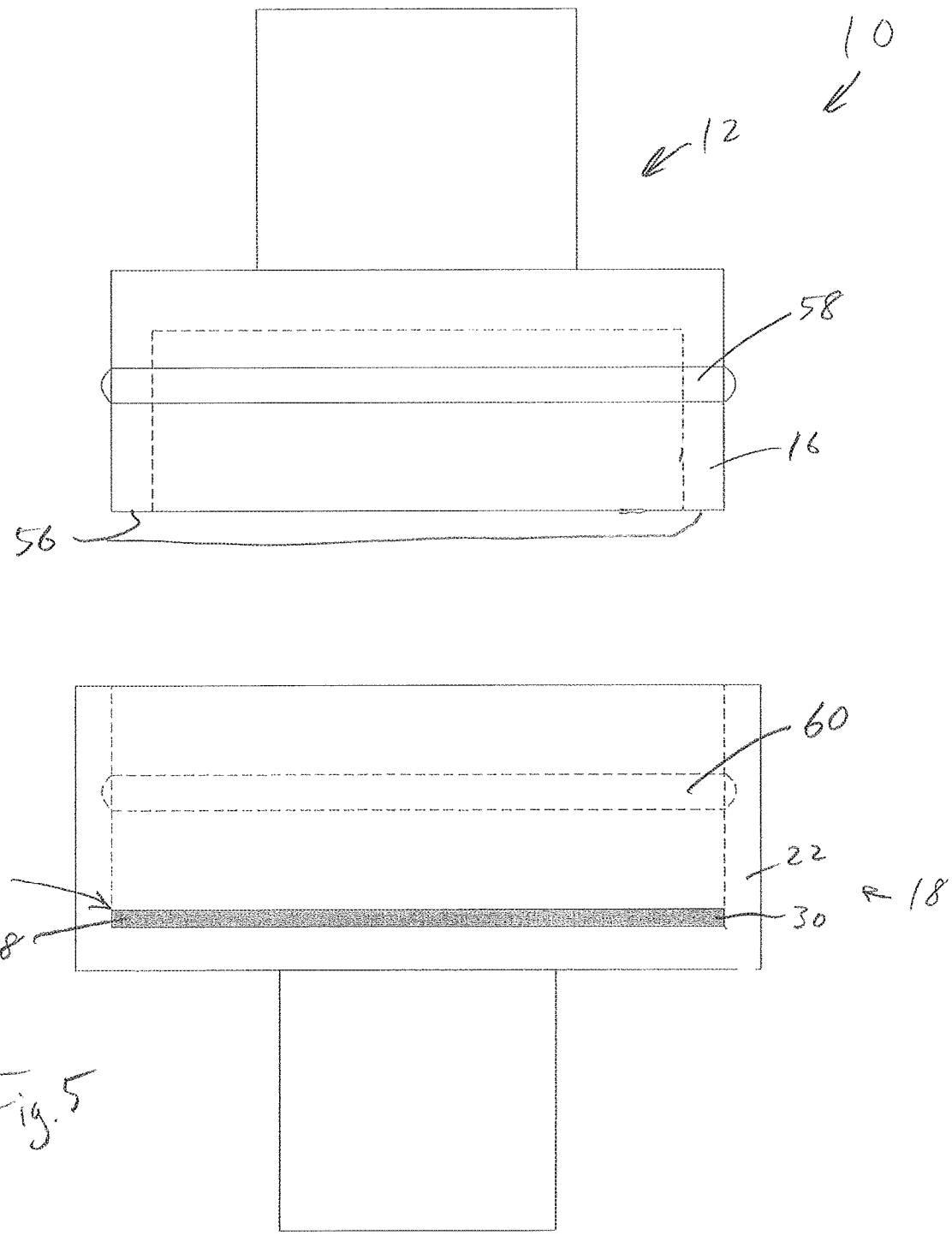
FIG. 5 is an exploded view of a CPR training device according to an embodiment of the present disclosure.

Referring now to FIG. 5, an embodiment of the device 10 includes the first engaging portion 16 having an annular protrusion 58 and the second engaging portion 22 having an annular recess 60 configured to receive the annular protrusion 58. The first engaging portion 16 and the second engaging portion 22 form the filter seating arrangement 26 at a filter seat position 28 when the first engaging portion 16 is inserted into the second engaging portion 22 of the device 10. The filter 30 is ultimately secured within the CPR training device 10 at the end surface 56 of the first engaging portion 16, as shown in FIG. 5.

Figure 6:
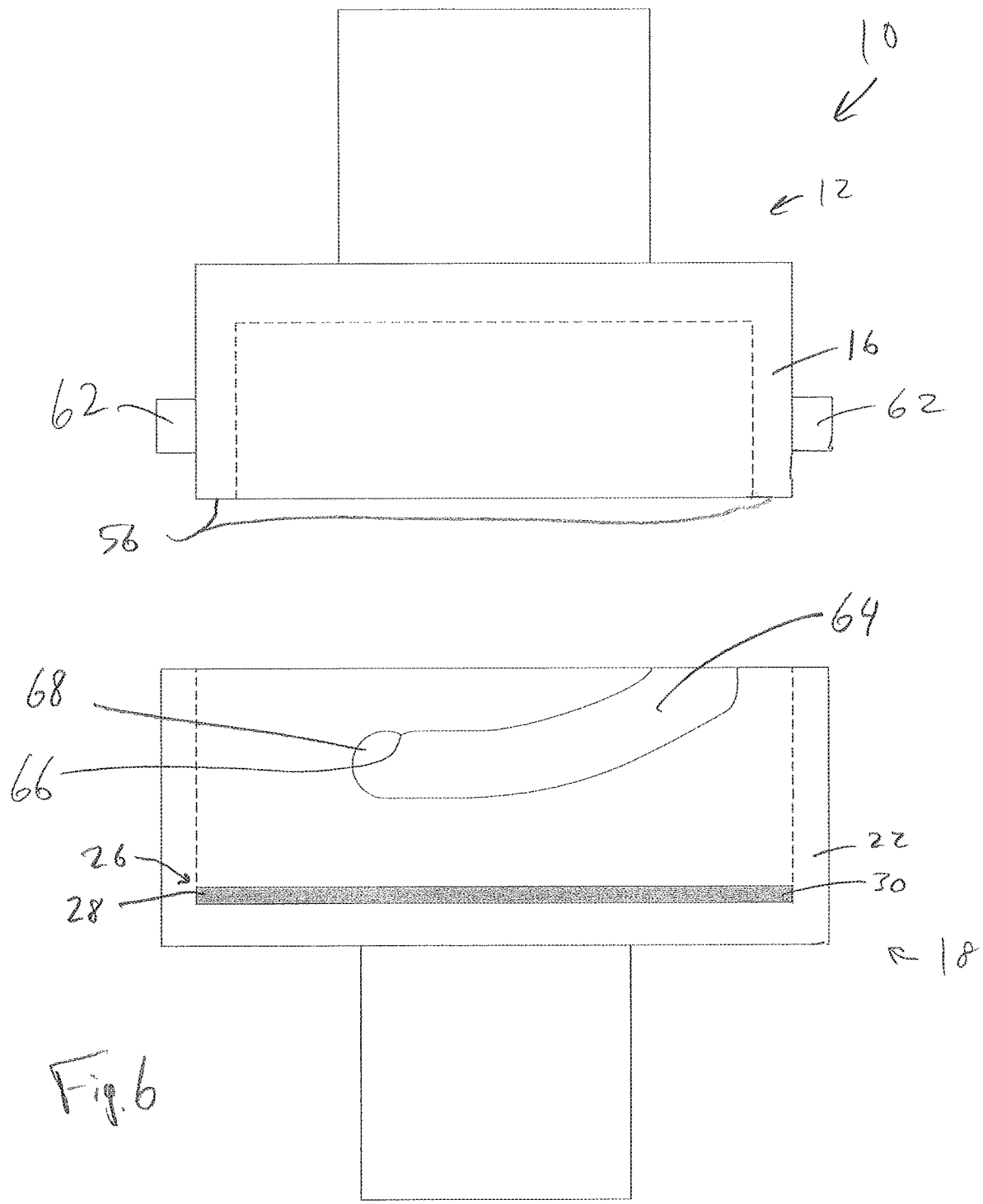
FIG. 6 is an exploded view of a CPR training device according to an embodiment of the present disclosure.

Referring now to FIG. 6, an embodiment of the device 10 includes the first engaging portion 16 having at least one radial protrusion 62 and the second engaging portion 22 having at least one slot 64 configured to receive the at least one radial protrusion 62. As shown in FIG. 6, the first engaging portion 16 of an embodiment includes two radial protrusions 62, and the second engaging portion 22 of the embodiment includes two slots 64. Each slot 64 are angled at least partially into the second engaging portion 22 with a locking point 66 near an end. 68 of ear h slot 64 such that the one or more radial protrusions 62 move in each slot. 64 until being secured at the end 68 of the slot 64. The first engaging portion 16 and the second engaging portion 22 form the filter seating arrangement 26 at a filter seat position 28 when the first engaging portion 16 is inserted into the second engaging portion 22 of the device 10. The filter 30 is ultimately secured within the CPR training device 10 at an end surface 56 of the first engaging portion 16, as shown in FIG. 6.

Figure 7:
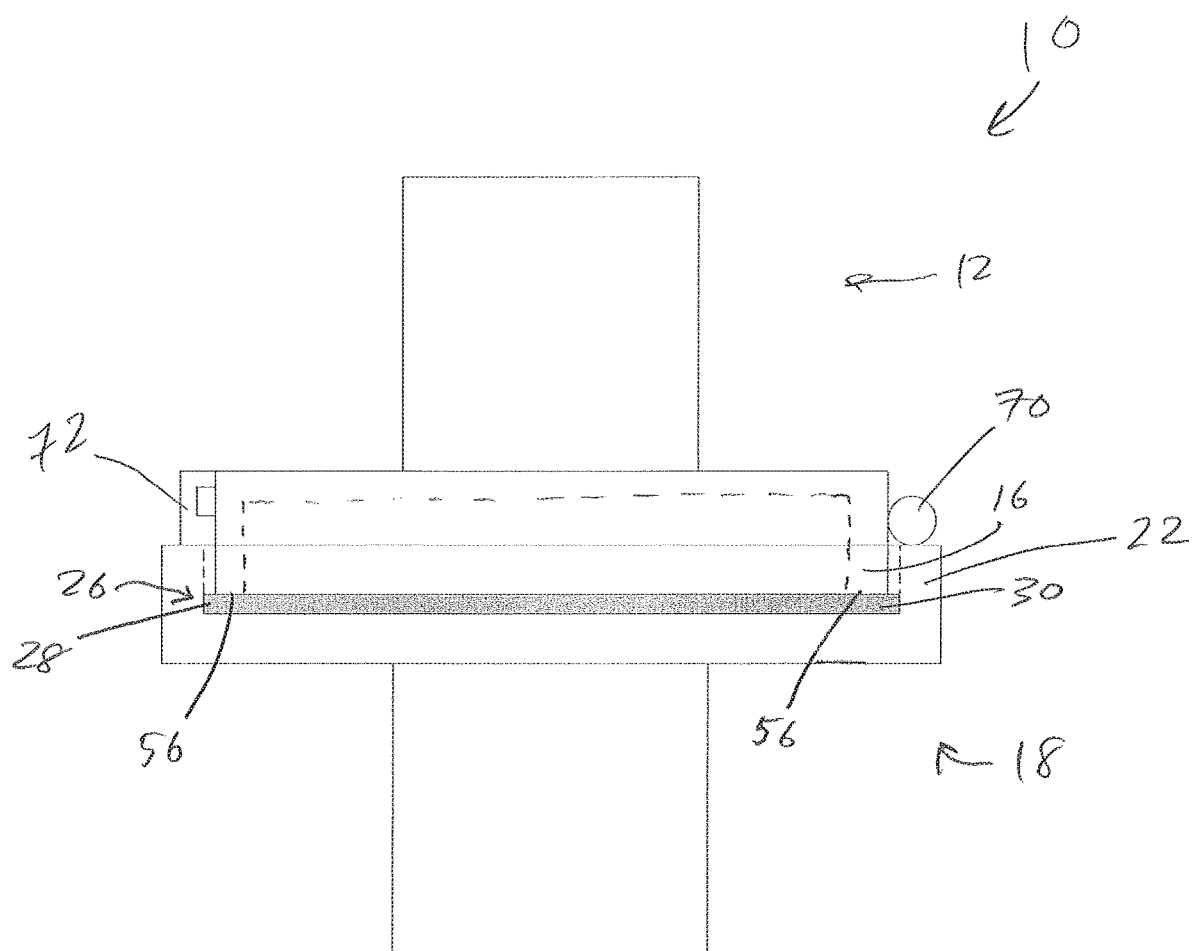
FIG. 7 is a side elevation view of a CPR training device according to an embodiment of the present disclosure.

Referring now to FIG. 7, an embodiment of the device 10 includes the first engaging portion 16 and the second engaging portion 22 being pivotally connected to each other with hinge 70. One or both of the first engaging portion 16 and the second engaging portion 22 includes a latch 72 to engage the other of the first engaging portion 16 and the second engaging portion 22. The latch 72 may include such structures or mechanisms as a hook, magnet(s), snap(s), button (s), or any similar structure or mechanism. The first engaging portion 16 and the second engaging portion 22 form the filter seating arrangement 26 at a filter seat position 28 when the first engaging portion 16 is inserted into the second engaging portion 22 of the device 10. The filter 30 is ultimately secured within the CPR training device 10 at an end surface 56 of the first engaging portion 16, as shown in FIG. 7.

Referring now to FIG. 8, an embodiment of the device 10 includes the first engaging portion 16 and the second engaging portion 22 engaging ach other an interference fit. The first engaging portion 16 includes an outer diameter 74 that is equal to or greater than an inner diameter 76 of the second engaging portion 22. One or both of the first engaging portion 16 and the second engaging portion 22 includes a chamfer or taper to allow the first engaging portion 16 to be press-fit into the second engaging portion 22. The first engaging portion 16 of the embodiment shown in FIG. 8 includes a tapered outer diameter 74 to allow fitting of the first engaging portion 16 into the second engaging portion 22. The first engaging portion 16 and the second engaging portion 22 form the filter seating arrangement 26 at a filter seat position 28 when the first engaging portion 16 is inserted into the second engaging portion 22 of the device 10. The filter 30 is ultimately secured within the CPR training device 10 at an end surface 56 of the first engaging portion 16, as shown in FIG. 8.

Figure 9:
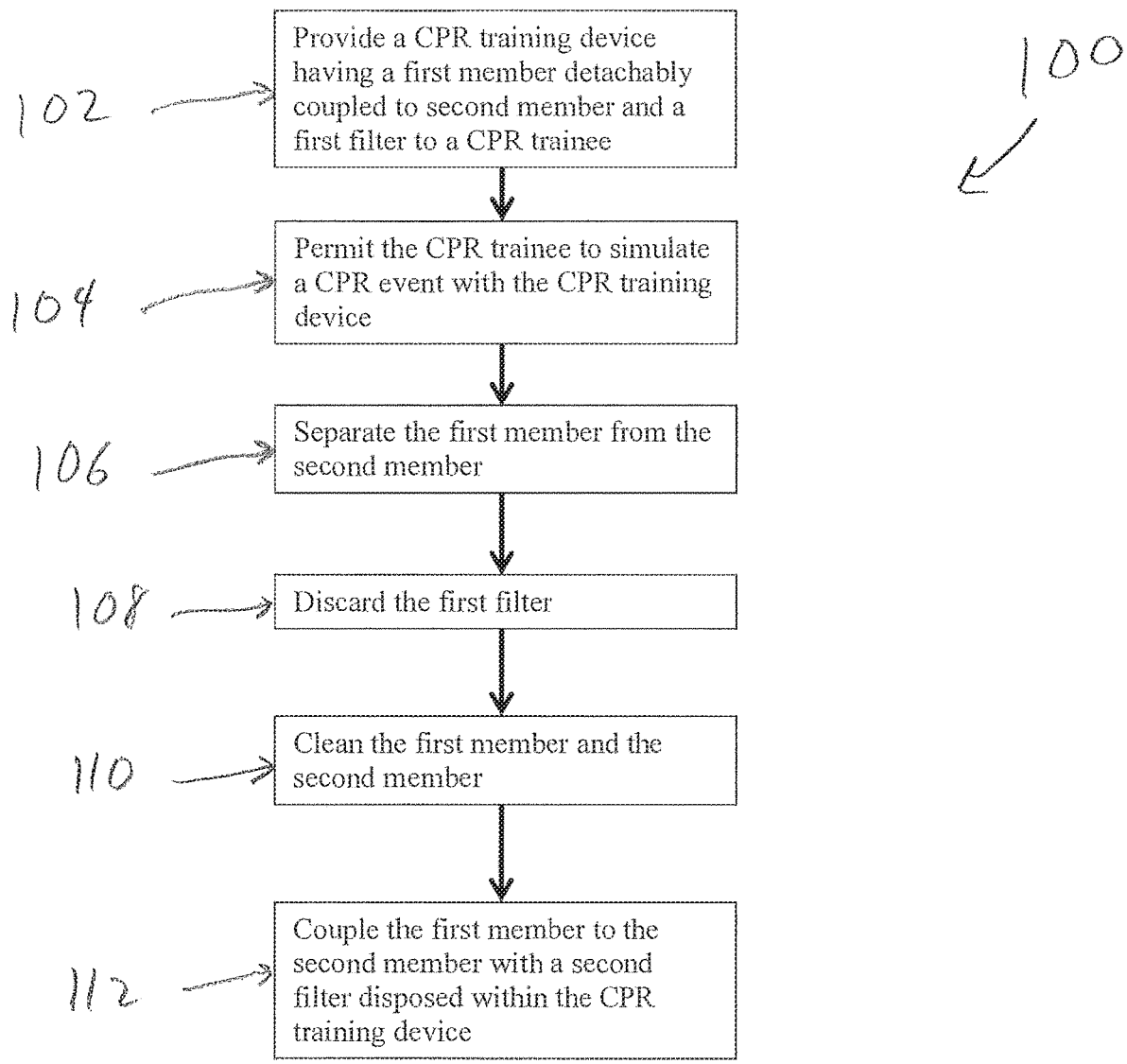
FIG. 9 illustrates a method of using a CPR training device according to an embodiment of the present disclosure.

Reference is now made to FIG. 9, which illustrates a method 100 of using the CPR training device 10. The method 100 includes providing, at step 102, the CPR training device 10 having the first member 12 detachably coupled to the second member 18 and a first filter disposed within the CPR training device 10 to a CPR trainee. The method 100 further includes permitting, at step 104, the CPR trainee to simulate a CPR event with the CPR training device. In one or more embodiments, simulating a CPR event includes engaging the mouthpiece portion 14 of the CPR training device 10 with a mouth. In one or more embodiments, simulating a CPR event includes engaging one of the CPR masks 34, 44 with the adapter portion 32 or the output portion 20 of the CPR training device 10. The method 100 further includes separating, at step 106, the first member 12 from the second member 18 and discarding, at step 108, the first filter 30. The method 100 further includes cleaning, at step 110, the first member and the second member and coupling, at step 112, the first member 12 to the second member 18 with a second filter disposed within the CPR training device 10.

In one or more embodiments, the cleaning at step 110 is performed in accordance with CDC guidelines by gently washing the first member 12 and the second member 18 in warm soapy water using dishwashing liquid. The first member 12 and the second member 18 are then rinsed with clean water and completely submerged into a disinfection solution of 0.25 cup unscented liquid chlorine bleach per gallon of water. The first member 12 and the second member 18 are then permitted to stand in a bleach and water solution for ten minutes, rinsed with fresh clean water, and air dried. In another embodiment, the first member 12 and the second member 18 are subjected to elevated temperatures necessary to disinfect using, in one non-limiting example, an autoclave. In another embodiment, the first member 12 and the second member 18 are cleaned in a dishwasher another embodiment of the present disclosure, a method does not include separating the first member 12 and the second member 18 and includes removing the first filter and inserting the second filter without separating the first member 12 and the second member 18. In such an embodiment, the device 10 includes a filter module that includes a filter that is capable of being removed without separation of the first member 12 and the second member 18, such as, in a non-limiting example, by sliding the filter module into and out of the device 10 through a side surface of the device 10.

The method 100 of additional embodiments of the present disclosure further includes the first member 12 being detachably coupled to the second member 18 using helical threads 50, as described in the embodiment of FIG. 4, the first member 12 including the annular protrusion 58 to detachably couple to the annular recess 60 of the second member 18, as described in the embodiment of FIG. 5, the first member 12 including the radial protrusion 62 to detachably couple to the slot 64 of the second member 18, as described in the embodiment of FIG. 6, the first member 12 including the latch 72 to detachably couple to the second member, as described in the embodiment of FIG. 7, and the first member 12 being detachably coupled to the second member 18 in an interference fit, as described in the embodiment of FIG. 8. In one or more embodiments, the first filter and/or the second filter comprises a paper material. In one or more embodiments, the first filter and/or the second filter comprises a fabric material.

The device 10 and methods of the present disclosure prevent contamination to and from a CPR trainee using the device 10. The device 10 and methods prevent germs and other contaminants from entering a CPR training lung, such as a manikin lung, or other training equipment and prevent germs and other contaminants in the training lung or other training equipment from reaching the CPR trainee. Additionally, the device 10 and associated methods allow a CPR training device that effectively simulates a CPR valve that is cleaned and reused by multiple CPR trainees.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this disclosure.

As shown in FIGS. 1, 2 & 3, mouthpiece portion 14 is a straight, elongate, and vertically oriented (relative to air passageway 24/axis 92) annular sidewall; first engaging portion 16 is a straight, elongate, and vertically oriented (relative to air passageway 24/axis 92) annular sidewall having surface 56 disposed on a distal end thereof; output portion 20 (and/or adapter portion 32) is a straight, elongate, and vertically oriented (relative to air passageway 24/axis 92) annular sidewall; second engaging portion 22 is a straight, elongate, and vertically oriented (relative to air passageway 24/axis 92) annular sidewall; and filter 30 is in a horizontal plane that is disposed vertically below first engaging portion 16. As shown FIGS. 1, 2, & 3, when assembled, first engaging portion 16 is adjacent to, and radially inside of, second engaging portion 22.

Referring now to FIGS. 2 & 3, a flat portion 180 of the first engaging portion 16 is disposed between an inner surface 170 of the mouthpiece portion 14 and an inner surface 160 of the first engaging portion 16, the flat portion 180 of the first engaging portion 16 being perpendicular to the inner surface 170 of the mouthpiece portion 14 and the inner surface 160 of the first engaging portion 16. As shown in FIGS. 2 & 3, the inner surface 160 of the first engaging portion 16 and the inner surface 170 of the mouthpiece portion 14 comprise sidewalls that are entirely straight, elongate, and vertically oriented (relative to air passageway 24/axis 92). As shown in FIGS. 2 & 3, the inner surface 170 of the mouthpiece portion 14 forms a smaller diameter opening relative to the inner surface 160 of the first engaging portion 16.

While this invention has been shown and described with respect to a detailed embodiment thereof, it will be understood by those skilled in the art that changes in form and detail thereof may be made without departing from the scope of the claims of the invention.

What is claimed is:
1. A method of using a CPR training device comprising:
   providing a CPR training device having a first member detachably coupled to a second member and a first filter disposed within said CPR training device to a CPR trainee or trainer;

wherein the CPR training device further comprises:
  said first member includes a first engaging portion having an inner surface, an outer surface, and a flat end surface therebetween,
  said second member includes a second engaging portion having an inner surface and an outer surface,
  said first member and said second member being reversibly attached, wherein the outer surface of the first engaging portion is engaged with the inner surface of the second engaging portion, whereby, when said first member and said second member are assembled such that the flat end surface of said first engaging portion secures the first filter against a flat portion of the inner surface of the second engaging portion, said first engaging portion and said second engaging portion cooperate to form a filter seating arrangement at a filter seat position along a horizontal plane;
  the inner surface of said first engaging portion comprising sidewalls that are straight, elongate, and vertically oriented relative to the flat end surface of said first engaging portion being entirely perpendicular to an air passageway defined by an interior space of the first member and second member;
instructing said CPR trainee or trainer to engage said CPR training device with a CPR mask;
instructing said CPR trainee or trainer to separate said first member from said second member;
instructing said CPR trainee or trainer to discard said first filter;
instructing said CPR trainee or trainer to couple said first member to said second member with a second filter disposed within said CPR training device.

2. The method of claim 1, wherein said first member is detachably coupled to said second member using helical threads.

3. The method of claim 1, wherein said first member includes an annular protrusion to detachably couple to an annular recess of said second member.

4. The method of claim 1, wherein said first member includes a radial protrusion to detachably couple to a slot of said second member.

5. The method of claim 1, wherein said first member includes a latch to detachably couple to said second member.

6. The method of claim 1, wherein said first member is detachably coupled to said second member in an interference fit.

7. The method of claim 1, wherein said first filter and said second filter comprise a paper material.

8. The method of claim 1, wherein said first filter and said second filter comprise a fabric material.

9. The method of claim 1 wherein
the first member includes a mouthpiece portion;
a flat portion of the first engaging portion is disposed between an inner surface of the mouthpiece portion and the inner surface of the first engaging portion, the flat portion of the first engaging portion being perpendicular to the inner surface of the mouthpiece portion and the inner surface of the first engaging portion, the inner surface of the mouthpiece portion forming a smaller diameter opening relative to the inner surface of the first engaging portion.

10. A method of using a CPR training device comprising:
providing a CPR training device having a first member detachably coupled to a second member and a first filter disposed within said CPR training device to a CPR trainee or trainer;
wherein the CPR training device further comprises:
  said first member includes a first engaging portion having an inner surface, an outer surface, and a flat end surface therebetween,
  said second member includes a second engaging portion having an inner surface and an outer surface,
  said first member and said second member being reversibly attached, wherein the outer surface of the first engaging portion is engaged with the inner surface of the second engaging portion, whereby, when said first member and said second member are assembled such that the flat end surface of said first engaging portion secures the first filter against a flat portion of the inner surface of the second engaging portion, said first engaging portion and said second engaging portion cooperate to form a filter seating arrangement at a filter seat position along a horizontal plane;
  the inner surface of said first engaging portion comprising sidewalls that are straight, elongate, and vertically oriented relative to the flat end surface of said first engaging portion being entirely perpendicular to an air passageway defined by an interior space of the first member and second member;
instructing said CPR trainee or trainer to engage said CPR training device with a CPR mask.

11. The method of claim 10 further comprising:
instructing said CPR trainee or trainer to separate said first member from said second member;
instructing said CPR trainee or trainer to discard said first filter;
instructing said CPR trainee or trainer to couple said first member to said second member with a second filter disposed within said CPR training device.

* * * * *